United States Patent [19]

Kem

[11] 4,396,556
[45] Aug. 2, 1983

[54] PROCESS OF PREPARING ORGANOPHOSPHORUS COMPOUNDS BY PHASE TRANSFER CATALYSIS

[75] Inventor: Kenneth M. Kem, San Juan Capistrano, Calif.

[73] Assignee: Occidental Research Corporation, Irvine, Calif.

[21] Appl. No.: 239,731

[22] Filed: Mar. 2, 1981

[51] Int. Cl.$^3$ .................... C07F 295/04; C07F 9/40
[52] U.S. Cl. ........................... 260/970; 260/239 B; 260/239 EP; 546/22; 548/413
[58] Field of Search ................ 260/970, 943, 239 EP, 260/239 B; 548/413; 546/22

[56] References Cited

U.S. PATENT DOCUMENTS

| | | | |
|---|---|---|---|
| 3,351,617 | 11/1967 | Jaeger et al. | 260/943 |
| 3,992,432 | 11/1976 | Napier et al. | 260/465.1 |
| 4,096,210 | 6/1978 | Freedman et al. | 260/973 |
| 4,192,796 | 3/1980 | Mosby et al. | 260/943 |

OTHER PUBLICATIONS

*Chemical Abstract*, 98:85742y of Eur. Pat. Appl. EP 31,761.
Kem, K. M.; Nguyen, N. V.; Cross, D. "Phase Transfer-Catalyzed Michaelis-Becker Reaction", *J. Org. Chem.*, 1981, 46, 5188.
Starks, "J.A.C.S.", vol. 93, No. 1, (1971), pp. 195-199.
Dehmlow, "Angew. Chem. Internat. Edit.", vol. 13, (1974) No. 3, pp. 170-179.
Petrov et al., Translation from "Zurnal Obshchei Khimii", vol. 30, No. 5, (1960), pp. 1602-1608.
Kosolapoff, G. M.; Maier, L. "Organic Phosphorus Compounds", Wiley-Interscience: New York, 1973; vol. 5, pp. 41-42.
Chemical Abstracts 59:12840(e).
Siddall, T. H.; Davis, M. A. "Simplified Preparation of Some Trisubstituted Phosphine Oxides", *J. Chem. Eng. Data*, 10(3), 303-305 (1965).

*Primary Examiner*—Anton H. Sutto
*Attorney, Agent, or Firm*—Barry A. Bisson

[57] ABSTRACT

Novel organic tertiary phoshine oxides and organic phoshonic acid esters, for example, bidentate organophosphorus actinide extractants, such as the carbamoylmethylphosphonates (CMP's) can be prepared (for example, in 90% or better yield and purity) by a process involving phase transfer catalysis, under conditions where degradive hydrolysis of the products or reactants is substantially avoided. For example, carbamoylmethylphosphonates can be prepared by reaction of the corresponding secondary phosphites with 2-substituted acetamides (wherever the substituent is a good leaving group, e.g. chlorine) in a two-phase system containing a high concentration of an aqueous base (preferably sodium hydroxide) and a suitable phase transfer catalyst, e.g., tetralkylammonium chlorides. Similarly, secondary phosphine oxides can be converted to novel tertiary carbamoylmethylphoshine oxides which are useful as extractants for transplutonium elements.

23 Claims, No Drawings

PROCESS OF PREPARING ORGANOPHOSPHORUS COMPOUNDS BY PHASE TRANSFER CATALYSIS

BACKGROUND

This invention involves an improved process for the preparation of organophosphorus compounds, e.g., tertiary phosphine oxides and phosphonate esters, such as dialkyl N,N-dialkylcarbamoylmethylphosphonates, which are useful as reagents for the fractionation of radionuclides (e.g., transplutonium elements) from nuclear process streams by solvent extraction (e.g., see U.S. Pat. No. 3,993,728 to Schultz) and/or for extracting uranium from wet process phosphoric acid.

One prior art process, based on the Arbuzov rearrangement, typically affords impure products in about 40% yield (see Siddall III, T. H., *J. Inorg. Nucl. Chem.*, 25, 883 (1963), while another, based on the Michaelis-Becker reaction, produces a similar product in about 40–60% yield (Ibid., 26, 1991 (1964)). The side reactions typical of these prior art methods are described by Petrov, et al, *J. Gen. Chem. U.S.S.R.*, 30, 1604 (1960), and are detrimental to the yields and to the product purities desired for these high boiling liquids. The present invention can allow high yield and purity, for example, of dialkyl phosphonates and trialkylphosphine oxides via a Michaelis-Becker reaction facilitated by liquid-liquid phase transfer catalysis (sometimes herein after called PTC). Phase transfer catalysis has been described, for example, by W. P. Weber and G. W. Gokel, *Phase Transfer Catalysis in Organic Synthesis*, Springer-Verlag, New York (1977), and by C. M. Starks and C. Liotta, *Phase Transfer Catalysis: Principles and Techniques*, Academic Press, New York (1978).

Hereinafter, sometimes, the following general equations and formulae will be referred to by the indicated number.

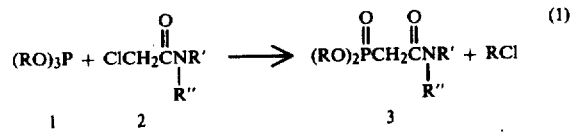

(1)

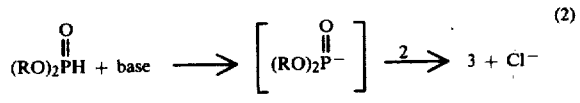

(2)

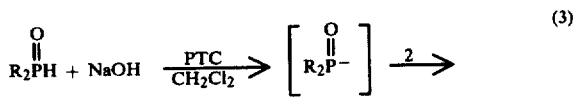

(3)

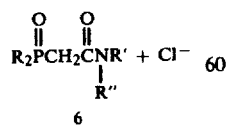

Siddall disclosed the reaction of trialkyl phosphites, of formula, 1, with N,N-dialkylchloroacetamides of formula, 2, (Eq. 1), to be sluggish, requiring forcing conditions (e.g., high temperatures). The reactivity of compounds of formula 1 is further reduced when R is large, as in the case of the preparation of solvent extraction reagents where hydrophobicity is required.

Although the nucleophilic displacement of compounds of formula 2 by alkali metal salts of dialkyl phosphites, of formula 4 (Eq. 2), occurs under considerably milder conditions, the necessary use of strong anhydrous bases, such as sodium metal (to generate the alkali metal salts), is inconvenient on a large scale and leads to side reactions of a magnitude similar to the former route.

M. Fedorynski, K. Wojciechowski, Z. Matacz, and M. Makosza, *J. Org. Chem.*, 43, 4682 (1978), and Polish Patent 105,428 (1980), *Chemical Abstracts*, 93:953994 reported that a reactive dialkyl phosphite, of formula 4 where R is $C_2H_5$, reacts with active alkylating agent benzyl chloride in the presence of potassium carbonate and tetrabutylammonium bromide at 100° C. to afford diethyl benzylphosphonate in 66% yield. It is likely that this reaction proceeds by proton abstraction on the surface of the solid carbonate, providing a means of alkylating reactive, but hydrolytically unstable dialkyl phosphites.

G. M. Kosolapoff and L. Maier, *Organic Phosphorus Compounds*, Vol. 5, Wiley Interscience, New York, pp 41–2 (1973), note that it is generally known that dialkyl phosphites are vulnerable to hydrolysis in aqueous environments, either acidic or basic.

SUMMARY OF THE INVENTION

The invention involves a process for preparing an organophosphorus compound of the formula (I):

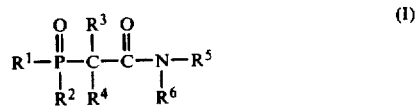

(I)

where $R^1$ and $R^2$ can be different or the same and are selected from alkyl, aryl alkoxyl containing at least 3 carbon atoms and aryloxyl, and where $R^1$ and $R^2$ can be in connection forming a ring structure; $R^3$, $R^4$, $R^5$ and $R^6$ can be different or the same and are selected from hydrogen, alkyl, or aryl, and where at least one of $R^3$ and $R^4$ is preferably hydrogen, and when $R^5$ and $R^6$ can be in connection forming a ring structure, said process comprising (a) reacting an organophosphorus compound of the formula (II) where $R^1$ and $R^2$ are defined as above:

(II)

with a 2-substituted alkanoic amide of the formula (III):

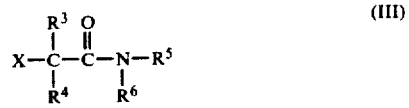

(III)

where X is a good leaving group, $R^3$, $R^4$, $R^5$ and $R^6$ are as defined above; and (b) conducting said reaction in a liquid-liquid, two-phase system comprising an aqueous phase containing a high concentration of an aqueous base and an organic phase containing a phase transfer catalyst and under reaction conditions such that degradive hydrolysis of the products or reactants is substantially avoided and such that said organophosphorus compound of formula (I) is a product of said reaction.

Preferably, the phase transfer catalyst is selected from quaternary ammonium compounds and quaternary phosphonium compounds, more preferred from compounds of the formula $(Z)_4NX'$ or $(Z)_4PX'$ where Z can be the same or different and is selected from alkyl groups containing 1-18 carbon atoms. Preferably no more than one Z group has fewer than 4 carbon atoms and X' is selected from chloride, perchlorate, hydrogen sulfate, bromide, and alkyl sulfonate. For example, one Z group can be an alkyl group containing less than 4 carbon atoms and the other three Z groups can be alkyl groups, which can be the same or different, containing at least 4 carbon atoms. For example, said catalyst can be selected from methyltricaprylammonium chloride, tetrabutylammonium chloride, tetrabutylammonium hydrogen sulfate, tetrahexylammonium chloride, and tetrabutylphosphonium chloride.

Leaving groups are described, for example, in J. March, *Advanced Organic Chemistry, Reactions, Mechanisms, and Structure*, pp. 290–94, McGraw Hill, N.Y. (1968). Usually, the best leaving groups are the weakest bases (in nucleophilic displacement reactions).

In the above-formulae, there is virtually no upper limit to the size of $R^1$ and $R^2$ (they can even be polymers of high molecuar weight), however, it is preferred that $R^1$ and $R^2$ be selected from: (1) alkyoxyl of at least 3 carbon atoms (except for alkoxyl groups which impart excessive water solubility to compounds of formula II), more preferred is a primary alkoxyl group of above about 4 to about 10 carbon atoms which can be branched or linear; (2) from alkyl groups of from about 1 to about 18 carbon atoms, more preferred a primary alkyl group of from about 1 to about 12 carbon atoms (which can be linear or branched); (3) from any aryloxy groups which do not impart excessive water solubility to compounds of formula II; and (4) from any aryl group that does not impart excessive water solubility to compounds of formula II. Preferably, both $R^1$ and $R^2$ are not aryl.

In contrast, if $R^3$ and $R^4$ are of excessive size a detrimental effect upon the reactivity of compounds of formula III is observed. Preferably, at least one of $R^3$ and $R^4$ is hydrogen with the other group being selected from alkyl groups of about 1 to about 18 carbon atoms (which can be linear or branched) as long as the group does not impart excessive water solubility to compounds of formula III.

One of $R^5$ and $R^6$ can be hydrogen, but preferably not both. One of $R^5$ and $R^6$ can be aryl, but preferably not both. $R^5$ and $R^6$ can be one or both selected from alkyl groups, preferably containing from about 1 to about 18 carbon atoms (which can be branched or linear) or can form a heterycyclic ring, preferably containing from about 3 to about 7 members including the amide nitrogen atom.

The process is especially useful for preparing carbamoylmethylphosphonates by reacting (i) a secondary phosphite ester of the formula (II), where $R^1$ and $R^2$ can be different or the same and are selected from alkoxyl- having at least 3 carbon atoms, or aryloxyl, (ii) with a 2-substituted alkanoic amide of the formula (III), where X is a good leaving group, $R^3$ and $R^4$ are hydrogen, and $R^5$ and $R^6$ are defined above.

For example, the 2-substituted alkanoic amide can comprise an N,N-dialkylchloroacetamide of the formula:

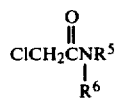

where $R^5$ and $R^6$ are the same or different and are alkyl groups of about 1 to about 18 carbon atoms or can form a heterocyclic ring preferably containing from about 3 to about 7 members including the amide nitrogen atom.

Where the secondary phosphite ester can be degraded by hydrolysis (such as when the ester has an R group containing about 3 to about 5 carbon atoms), it is preferred that it be present in stoichiometric excess (e.g. about 1% to about 40% excess) relative to the acetamide.

For example, the process is useful for preparing di(n-hexyl) N,N-diethylcarbamoylmethylphosphonate (that is structure (I), where $R^1 = R^2 =$ n-hexoxy, $R^3 = R^4 =$ hydrogen, and $R^5 = R^6 =$ ethyl) of the formula (Ia):

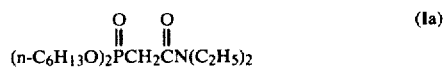 (Ia)

by reacting di(n-hexyl) phosphite (IIa), that is, the structure (II), where $R^1 = R^2 =$ n-hexoy, with N,N-diethylchloroacetamide (IIIa), that is, formula (III), where X=Cl, $R^3 = R^4 =$ hydrogen, and $R^5 = R^6 =$ ethyl.

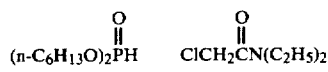

(IIa)      (IIIa)

wherein the reaction is conducted at a temperature in the range of about $-20°$ C. to about 50° C. (more preferred about 0° C. to about 30° C.) in a liquid-liquid two-phase system comprising methylene chloride and an aqueous solution substantially saturated (e.g., about 50 weight percent at 10° C.) with respect to sodium hydroxide, the reaction being continued for sufficient time for the compound of formula (IIIa) to substantially completely react with the compound of formula (IIa), (a stoichiometric excess of either compound can be present) to produce a reaction mixture containing the organophosphorus compound of formula (Ia) and for insufficient time for the organophosphorus compound of formula (Ia) to be degraded, as by hydrolysis; and, recovering the organophosphorus compound of formula (Ia) from the reaction mixture.

One embodiment of the present invention involves the surprising discovery, that a reactive dialkyl phosphite 4, where R is sufficiently large to afford good organic solubility (R is greater than or equal to $C_3H_7$), exhibits reasonable stability in an organic-aqueous two-phase system. This observation permits the application of typical phase transfer catalysis with aqueous sodium hydroxide to the Michaelis-Becker reaction.

According to the invention, organic phosphonic acid esters, for example, bidentate organophosphorus actinide extractants, such as the carbamoylmethylphosphonates (CMP's), and novel organic tertiary phosphine oxides such as carbamoylmethylphosphine oxides of formula 6 can be prepared by a process involving phase transfer catalysis, under conditions where degradative hydrolysis of the products and reactants is substantially avoided. For example, carbamoylmethylphosphonates can be prepared by reaction of the corresponding secondary phosphites with 2-substituted acetamides (wherever the 2-substituent is a good leaving group, e.g. chlorine) in a two-phase system containing a high concentration of an aqueous phase (preferably sodium hydroxide) and a suitable phase transfer catalyst, e.g., tetraalkylammonium chlorides. Similarly, secondary phosphine oxides can be converted to novel tertiary carbamoylmethylphosphine oxides which are useful as extractants for transplutonium elements and for recovering uranium from phosphoric acid.

The inventon also involves reaction conditions to favor nucleophilic displacement (Eq. 2) relative to consumption of 4 by hydrolysis, whereby excellent yields of dialkyl N,N-dialkylcarbamoylmethylphosphonates 3 are obtained under very mild and convenient conditions (see Table I). The invention also involves alkylation of the less reactive dialkylphosphine oxides, 5 (Eq. 3), whose good hydrolytic stability permits higher reaction temperatures.

FURTHER DESCRIPTION

Agitation of a two-phase system comprised of an aqueous base, such as sodium hydroxide solution and an organic phase preferably made up of a solvent (although the solvent can be omitted), such as methylene chloride, the reactants, 2 and 4, and a catalytic amount of a quaternary ammonium chloride, (Z)$_4$NCl, enables ion exchange between (Z)$_4$NCl and the sodium hydroxide to occur at the phase interface with distribution of the resultant base, (Z)$_4$NOH, to the organic phase (Eq. 4). There, it is a sufficiently strong base to deprotonate the dialkyl phosphite, 4, (Eq. 5).

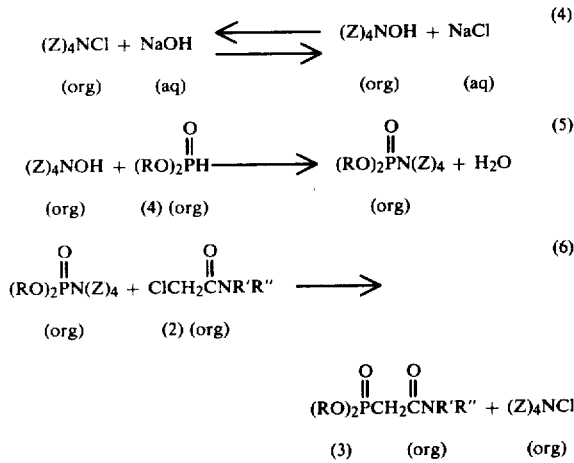

The nucleophilic phosphite anion [(RO)$_2$PO$^-$] reacts as it is formed with 2 to form the product 3, directly (Eq. 6). The avoidance of high concentrations of the phosphite anion is likely the reason (along with the mild conditions) that side products typical of conventional Michaelis-Becker reactions (Eq. 7 and 8) are nearly excluded by this technique (see Petrov, et al., Ibid.).

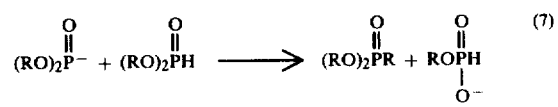

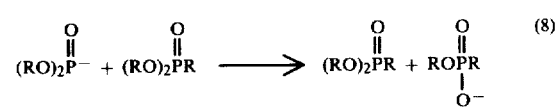

Hydrophobic aliphatic quaternary ammonium chlorides are the catalysts preferred for favorable organic phase distribution of (Z)$_4$NOH, necessary for effective hydroxide transfer (Eq. 4). Additionally, such hydrophobic character of the catalyst enhances organic phase distribution of the phosphite anion (Eqs. 5 and 6), minimizing hydrolytic degradation. The structural features of the catalysts which are conducive to PTC (i.e., phase transfer catalysis) activity in general and which can be used in the process include, for example, those disclosed in the books by Weber and Gokel and by Starks and Liotta (Ibid.).

The preferred catalysts are transfer agents for anions, e.g., hydroxide ions. Typical catalysts include quaternary ammonium compounds of the structure (Z)$_4$N$^+$X$^-$, where Z is alkyl or aryl, preferably alkyl of 1-18 carbon atoms (for example: tetrabutylammonium hydrogen sulfate, methyltricapyrylylammonium chloride) and quaternary phosphonium compounds of the structure (Z)$_4$P$^+$X$^-$, where R is defined as above (for example, tetrabutylphosphonium bromide or chloride, hexadecyltributylphosphonium bromide or chloride) and where X is a counterion such as Cl$^-$, Br$^-$, or HSO$_4^-$. For further examples, including arsoniums, crown ethers, etc., see Weber and Gokel (Ibid.) and Starks and Liotta (Ibid.).

In the above catalyst formulae, Z can be the same or different, but is is preferred that no more than one Z group have less than 4 carbon atoms. If, for example, one Z group is large (say 16 carbon atoms) and the other three small (1 carbon atom), the compound can have undesirable surface activity (e.g., a cationic surfactant) and can cause emulsion problems and facilitate micellar hydrolysis. In practice, preferred catalysts include methyl tricaprylylammonium chloride (Aliquat 336 of General Mills Chem., or Adogen 464 of Ashland Chem.), tetrabutylammonium hydrogen sulfate, tetrabutylammonium chloride, tetrahexylammonium chloride, tetrabutylphosphonium chloride, etc.

The catalysts can be immobilized on a polymer matrix, as in an ion-exchange resin, so that a triphase catalyst system is employed, see for example, S. L. Regen, *Angew. Chem. Int. Ed. Engl.* 18, 421(1979).

In the above catalyst formulae, X$^-$ can be any anion, but should prefer the aqueous phase and should not associate too strongly with the quaternary ion, (Z)$_4$N$^+$.

Examples of the more preferred counterions (i.e., anions) include
Cl$^-$ (chloride), ClO$_4^-$ (perchlorate),
and HSO$_4^-$ (hydrogen sulfate).

Examples of others that can be useful include Br$^-$ (bromide, Y'SO$_3^-$, preferably where Y is an alkyl or alkoxyl group of one to four carbon atoms.

If the counterion (X)$^-$ associates with the quaternary ion in large preference to hydroxide, the catalyst is unavailble for OH$^-$ transfer, and thus is "poisoned."

Similarly, the anion generated by the displacement (i.e., the leaving group) should not "poison" the catalyst (see catalyst counterion selection preferences).

The leaving ability and degree of association with quaternary ions of halide leaving groups is:
$Cl^- < Br^- < I^-$ (leaving ability)
$Cl^- < Br^- < I^-$ (degree of association with quaternary)

Degree of association of the leaving groups with the quaternary ion is more important than its leaving ability; therefore $Cl^-$ is most preferred, bromide is also preferred and $I^-$ is less preferred because of possible catalyst "poisoning". Other preferred anions include, for example, $YSO_3^-$, where Y is an alkyl group of 1 to 4 carbon atoms, which is likely to associate which $(Z)_4N^+$ in the organic phase and, therefore, should prefer the aqueous phase after displacement (as should the counterion). Typical useful leaving groups are those described in J. March, *Advanced Organic Chemistry, Reactions, Mechanisms, and Structure*, pp. 290–94, McGraw Hill, N.Y. (1968).

Chloride is preferred for both the catalyst counterion and for the leaving group of the compounds of formula 2. It exchanges readily with other anions such as hydroxide ion and leads to a favorable equilibrium constant for equation 4. Less preferred anions such as $I^-$, or $Y'SO_3^-$ where Y' is an alkyl or alkoxyl group of greater than 4 carbon atoms and (to a less extent $Br^-$) can associate very strongly with $(Z)_4N^+$ in the organic phase (Starks and Liotta, Ibid., p. 67) and diminish its ability to transfer hydroxide ion, so catalyst "poisoning" can result from the presence of such anions.

If the catalyst, $(Z)_4NCl$, is replaced by a tertiary amine such as tri(n-butyl)amine, only hydrolysis of the compounds of formula 4 is observed. Tertiary amines do not catalyze the desired reaction.

Removal of the catalyst from the product can be accomplished by known techniques (e.g., see Starks and Liotta, page 55, and L. Rafecas and J. J. Artus, *Tetrahedron Lett.*, 21, 977 (1980)). Alternatively, the quaternary ammonium chloride used can be immobilized on an insoluble polymer matrix to form a solid-liquid-liquid triphase catalysis system in which the solid catalyst is easily removed by filtration (S. L. Regen, *Angew. Chem. Int. Ed. Engl.*, 18, 421 (1979)).

The degree of agitation is important to the success of the reaction. When a conventional laboratory mechanical paddle stirrer is used, the rate of reaction is proportional to the rate of stirring below about 200 rpm, due likely to a mass transfer effect. Above this point, however, the rate of reaction is independent of stirring rate, a common feature of PTC reactions. The rate of micellar hydrolysis, however, continues to increase rapidly with increased agitation, so it is advantageous to maintain the stirring speed near 200 rpm to minimize hydrolysis relative to the desired displacement reaction. The optimum degree of agitation is a function of the reactor combination, agitation method and reaction conditions and should be determined experimentally for any given case.

High aqueous phase salt concentrations favor hydroxide transfer (Eq. 4) and reduce aqueous phase distribution of all the organic species, reducing the tendency toward hydrolysis. This also reduces the amount of water available for hydration of the organic ions in the organic phase. Preferably, the ionic strength of the aqueous phase should be at least as great as that of a 25% by weight solution of sodium hydroxide in water. Commercial 50% sodium hydroxide is a more preferred aqueous phase, more dilute solutions lead to measurable hydrolysis. Other useful salts include mixtures of sodium hydroxide and sodium chloride or sodium sulfate. The primary consideration is to pick a salt whose anion does not poison the catalyst, but which increases the ionic strength of the aqueous phase and provides hydroxide ion for transfer to the organic phase.

Although the use of an organic solvent is not necessary (i.e., bulk phase reaction), best results have been obtained with the use of methylene chloride. This solvent appears to facilitate hydroxide transfer, diminishes organic ion hydration in the organic phase, and provides favorable distribution coefficients for the organic species involved. Other useful solvents are described in the books by by Weber and Gokel and by Starks and Liotta (Ibid.).

Hydrophobic R groups naturally improve the organic distribution of compounds of formula 4, of the phosphite anion, and of the product, of formula 3, reducing the chance for hydrolysis. This feature makes this technique ideally suited for the preparation of solvent extraction reagents for which such hydrophobicity is desirable.

Although under the properly chosen conditions, excellent yields of the product of formula 3 are obtained, excessive reaction times are to be avoided because product degradation in the reaction media can occur. It is not clear whether this decomposition is due to hydrolysis (Eq. 9) or to other reactions initiated by deprotonation of the methylene group (Eq. 10).

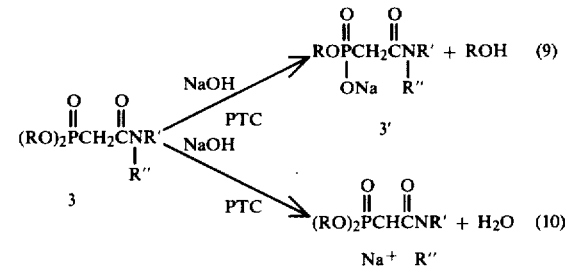

If hydrolysis occurs to any extent during the reaction, regardless of whether the hydrolyzed species is the starting phosphite, a compound of formula 4, phosphite anion, or a product of formula 3, a product of the hydrolysis is an alcohol, ROH.

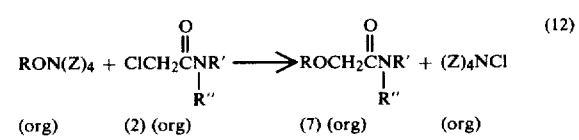

In the PTC system, the corresponding alkoxide of $(Z)_4NOH$ is formed (Eq. 11) which competes for the remaining chloroacetamide of formula, 2, resulting in irreversible formation of a by-product etheramide of formula, 7 (Eq. 12). It is also very likely that the phosphorus-containing hydrolysis product is an organic anion which strongly associates in the organic phase with $(Z)_4N^+$. Such catalyst "poisoning" (vide supra) results in reaction failure. The overall result is that the PTC route to the product of formula 3 either works exceptionally well, or it fails. Clearly, hydrolysis must be avoided.

In a reagent for use in solvent extraction, the presence of hydrolyzed products such as the compound of formula 3' or its conjugate acid cause serious problems (see Schultz and McIsaac, *Proc. Int. Solvent Extr. Conf.* 1977, *CIM Spec.*, Vol. 21, 619 (1979), and S. Katz and W. D. Bond, *J. Inorg. Nucl. Chem.*, 41, 1781 (1979)). Their very high extractant strength of compounds of formula 3' interferes with proper selective stripping. These hydrolyzed products are present in products, of formula 3, prepared by conventional routes (Eqs. 7 and 8) and can result from thermal or radiolytic decay during operation. The avoidance of these by-products relative to conventional techniques by the PTC route is a significant advantage.

The present invention provides a route to trialkylphosphine oxides of formula, 6, which are expected to be stronger extractants than the products of formula 3, in addition to being more stable to hydrolytic, radiolytic, and thermal conditions. Sodium salts of dialkylphosphine oxides are known to be very insoluble, a problem which generally precludes the use of the Michaelis-Becker reaction for the synthesis of trialkylphosphine oxides because the conventional technique involves stoichiometric formation of the salts (see T. H. Siddall III and M. H. Davis, *J. Chem. Eng. Data*, 10, 303 (1965)). However, no difficulties with precipitation are encountered during the PTC reaction, suggesting that the quaternary ammonium salts of formula 5 have sufficient solubility at the catalytic concentrations generated in the course of the reaction.

Use of cyclohexene as the reaction solvent leads to a normal reaction; no products indicative of the intermediacy of a carbene resulting from geminal dehydrochlorination of a compound of formula 2 could be detected (Eq. 13).

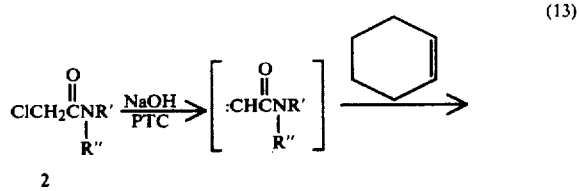

(13)

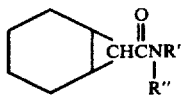

ILLUSTRATIVE EXAMPLES

In the following examples, a Perkin Elmer Sigma I Gas Chromatograph with a flame-ionization detector was used routinely for reaction monitoring and product analysis. A 6'×⅛" stainless steel column packed with 3% SE-30 on Chromsorb Q 80/100 was used with helium carrier. Temperature program and carrier gas flow rates were appropriate for the particular analysis. Carefully fractionated, chromatographically pure dibutyl phthalate was used as an internal standard for the quantitative analyses. Nuclear magnetic resonance (NMR) spectra were obtained from 20% solution in $CDCl_3$ with a Nicolet NT-200 spectrometer operated at 200.067 MHz for $^1H$ and at 80.98 MHz for $^{31}P$. The $^1H$ spectra of 3 and of 6 are unambiguous, the $CH_2$ signal appearing as a sharp doublet (Table II). The proton decoupled $^{31}P$ spectra consists of a sharp singlet (Table II) affording an excellent method of determining phosphorus-containing impurities. Methyltricaprylylammonium chloride was an 85% active commercial product of Ashland Chemicals (Adogen 464). Tributyl phosphite was a commercial product of Mobil Chemicals which was 89.1% tributyl phosphite, 1a, and 3.5% dibutyl phosphite, 4a, by gas-liquid chromatography (GLC). Dibutyl phosphite and di(2-ethylhexyl) phosphite were also products of Mobil Chemicals and were 93.8 and 93.6% pure by GLC. The diakyl phosphites which are not commercially available can be prepared by known procedures (for example, those procedures taught in: K. Schimmelschmidt and H. Kleiner, U.S. Pat. No. 3,725,515 (1973), G. M. Kosolapoff and L. Maier, *Organic Phosphorous Compounds*, Vol. 5, Wiley Interscience, New York, 40 (1973), and C. F. Baranauckas and J. J. Hodan, U.S. Pat. No. 3,331,895 (1967). N,N-dibutylchloroacetamide, N-(2-ethylhexyl)chloroacetamide, and N-chloroacetylpyrrolidine were prepared by the procedure described by W. E. Weaver and W. M. Whaley, *J. Am. Chem. Soc.*, 69, 515 (1947) and were 99.5+% by GLC. N,N-diethylchloroacetamide was obtained from ICN/K&K Life Sciences and was 97.7% by GLC. Di(n-butyl)phosphine oxide was obtained from Organometallics, Inc. and was 90% by GLC. Di(n-octyl)phosphine oxide was obtained from Specialty Organics, Inc. and was chromatographically pure. All other organics utilized were available from common sources and were of reagent quality. Elemental analyses were performed by Galbraith Labs., Inc., Knoxville, Tenn.

In the following examples and tables, R groups for specific structural formula (3 and 6) are indicated by letters as follows:

a. $R = n-C_4H_9$; $R' = R'' = C_2H_5$ b. $R = R' = R'' = n-C_4H_9$ c. $R = n-C_6H_{13}$; $R' = R'' = C_2H_5$ d. $R = (CH_3)_3CCH_2CHCH_2$; $R' = R'' = CH_3$
   |
   $CH_3$ e. $R = n-C_4H_9CHCH_2$; $R' = R'' = CH_3$
   |
   $C_2H_5$ f. $R = n-C_8H_{17}$; $R' = R'' = CH_3$ h. $R = n-C_4H_9CHCH_2$; $R' = R'' = C_2H_5$
   |
   $C_2H_5$ i. $R = n-C_8H_{17}$; $R' = R'' = C_2H_5$ j. $R = (CH_3)_3CCH_2CHCH_2CH_2$; $R' = R'' = CH_3$
   |
   $CH_3$ k. $R = i-C_9H_{19}$; $R' = R'' = CH_3$ l. $R = (CH_3)_2CH(CH_2)_3CHCH_2$; $R' = R'' = CH_3$
   |
   $CH_3$

| g. R = n-C₄H₉CHCH₂; R', R" = (CH₂)₄<br>  \|<br>  C₂H₅ | m. R = R' = n-C₄H₉CHCH₂; R" = H<br>  \|<br>  C₂H₅ |

EXAMPLE I

This example illustrates a prior art based on the Arbuzov rearrangement.

Preparation of dialkyl N,N-dialkylcarbamoylmethylphosphonates, 3. Method A.

Into a 500 ml three-necked, round-bottom flask equipped with a thermowell, a mechanical stirrer, and a 25 cm Vigreux distillation column surmounted by a stillhead and condenser, were placed 62.6 g (0.25 mole) of tributyl phosphite, 37.5 g of N,N-diethylchloroacetamide (0.25 mole), and 200 ml of dimethylformamide. The solution was heated to 150° C. with a mantle. After 12 hours of stirring at this temperature, 11.6 g of distillate had been collected (23.2 g C₄H₉Cl, theoretical). The solution was maintained under these conditions for an additional 24 hours, but no further condensate was observed. Evaporation in vacuo yielded 77.8 g (101%) of a brown oil which was 51% 3a by GLC. A major impurity (15%) was dibutyl butylphosphonate. Observable impurities eluted immediately before and after the product.

EXAMPLE II

This example illustrates a prior art process, based on the Michaelis-Becker Reaction.

Preparation of dialkyl N,N-dialkylcarbamoylmethylphosphonates, 3. Method B.

Into a 500 ml three-necked, round-bottom flask fitted with a mechanical stirrer, a reflux condenser surmounted by a gas bubbler, a 125 ml pressure-equalizing addition funnel, and inert gas fittings, were placed 200 ml of dry dimethylformamide, 50.6 g (0.25 mole) of dibutyl phosphite, and 13.5 g (0.25 mole) of anhydrous sodium methoxide. The mixture was stirred under a nitrogen atmosphere and maintained at 20°-25° C. After two hours, 37.5 g (0.25 mole) of N,N-diethylchloroacetamide dissolved in 50 ml of dry dimethylformamide was added dropwise over a period of 30 minutes. The mixture was heated slowly to 110° C. by a mantle and maintained at that temperature with stirring for four hours. After cooling, the mixture was suction filtered and evaporated in vacuo. The residual oil was dissolved in 150 ml of ether, washed with two 100 ml portions of water followed by 100 ml of saturated sodium chloride solution, and dried over anhydrous magnesium sulfate. Filtration and evaporation of the filtrate in vacuo yielded 54.4 g (71%) of an amber oil which was 39% 3a by GLC. A major impurity (16%) was dibutyl butylphosphonate. Impurities eluting immediately before and after the product were much less prominent than in Method A.

EXAMPLE III

This example illustrates a novel, improved process which combines certain features of the processes of Examples I and II.

Preparation of dialkyl N,N-dialkylcarbamoylmethylphosphonates, 3. Method C.

Into a 500 ml three-necked, round-bottom flask fitted with a thermowell, a mechanical stirrer, a 25 cm Vigreux distillation column surmounted by a still-head, condenser, and gas bubbler, a 125 ml pressure equalizing addition funnel, and inert gas fittings, were placed 66.9 g of commercial tributyl phosphite which was 89.1% tributyl phosphite and 3.5% dibutyl phosphite, 0.65 (0.012 mole) of anhydrous sodium methoxide, and 200 ml of dry dimethylformamide, under a nitrogen atmosphere. After stirring at 20°-25° C. for 15 minutes, 51.7 g (0.25 mole) of N,N-dibutylchloroacetamide in 50 ml of dry dimethylformamide was added. The temperature was maintained and stirring continued for one hour after which the mixture was heated to 120° C. by a mantle. After 4.5 hours, distillation had subsided with a total of 12.0 g of distillate collected (theo. 22 g of C₄H₉Cl). The mixture was allowed to cool, then filtered by suction. The filtrate was poured into a 1 liter separatory funnel containing 250 ml of ether and 250 ml of water. After equilibration, the aqueous layer was extracted with 150 ml of ether and the combined ether layers washed with 150 ml of water followed by 150 ml of saturated sodium chloride solution. The ether solution was dried over anhydrous magnesium sulfate, filtered, and evaporated in vacuo to yield 4.5 g (104%) of an amber oil which was 55% 3b. By-product dibutyl butylphosphonate was 7.3% and no prominent impurities eluted near the product.

EXAMPLE IV

Example IV illustrates the process of the present invention.

Preparation of dialkyl N,N-dialkylcarbamoylmethylphosphonates, 3, and dialkyl(N,N-dialkylcarbamoylmethyl)phosphine oxides, 6. Method D.

Into a 500 ml three-necked, round-bottom flask equipped with a thermowell, a 125 ml pressure-equalizing addition funnel, a mechanical stirrer, inert gas fittings, and a septum, were placed a solution of 21.36 g (0.10 mole) of distilled N,N-dibutylchloroacetamide and 0.5 g of methyltricaprylylammonium chloride in 75 ml of methylene chloride along with 100 ml of 50% sodium hydroxide. The solution was stirred at 200 rpm under a gentle purge of nitrogen and cooled to 5° C. by an ice bath. The solution was maintained at 5°-8° C. while a solution of 21.34 g (0.10 mole) of dibutyl phosphite and 0.5 g of methyltricaprylylammonium chloride in 75 ml of methylene chloride was added dropwise. Analytical samples were removed by syringe every 30 minutes for GLC analysis to follow the reaction progress by monitoring disappearance of starting material and formation of product. The addition was complete after one hour. In another two hours, dibutyl phosphite was exhausted, but 7% N,N-dibutylchloroacetamide remained; 3b product was 85%. Additional dibutyl phosphite, 8.6 g (0.04 mole) was added, stirring continued for two more hours, and the phases separated. The aqueous layer was extracted with 50 ml of pentane and the combined organic layers were washed with three 50 ml portions of pentane and the combined organic layers were washed with three 50 ml portions of water followed by one 50 ml portion of saturated sodium chloride solution. After drying over anhydrous potassium carbonate, and filtering, the filtrate was evaporated in vacuo (80° C.; 2 mm Hg). The nearly colorless oil weighed 30.8 g (100%) and was 91% 3b by GLC. No observable impurities eluted near the product, and no dibutylbutylphosphonate could be detected.

The above procedure was repeated using various starting materials, catalysts, proportions and reaction conditions as shown in Table I. The products of these runs are reported in Table I and are characterized in Table II. These Tables also report, for comparative purposes, results of Examples I, II, and III.

EXAMPLE V

This example illustrates one method of determining adverse reaction conditions, e.g. those leading to excess hydrolysis of a desired product. Such experiments can aid in establishing reaction conditions which avoid degrative hydrolysis of desired products.

Reaction Conditions Leading to Hydrolysis.

A reaction was conducted by the same general procedure as the PTC route described in Example IV. However, the reaction temperature was increased to 25° C.

TABLE I

Summary of Preparative Data for Products 3 and 6.[a]

| Product | Method | 1 (mole) | 2 (mole) | 4 (mole) | 5 (mole) | Catalyst (conc)[b] | Temp. (°C.) | Time (hr) | Crude Yield (%) | Crude Purity (%)[c] |
|---|---|---|---|---|---|---|---|---|---|---|
| 3a | A | 0.25 | 0.25 | — | — | — | 150 | 12 | 101 | 51 |
|  | B | — | 0.25 | 0.25 | — | — | 110 | 4 | 71 | 39 |
| 3b | C | 0.25 | 0.25 | — | — | — | 25;120 | 1;4.5 | 104 | 55 |
|  | D | — | 0.10 | 0.14 | — | A(2) | 5–10 | 5 | 100 | 91 |
| 3c | D | — | 0.25 | 0.25 | — | A(2) | 10–15 | 2.5 | 100 | 81 |
| 3d | D | — | 0.10 | 0.10 | — | A(2) | 15–20 | 3 | 79 | 84 |
| 3e | D | — | 0.10 | 0.10 | — | A(2) | 15–20 | 4.5 | 90 | 83 |
| 3g | D | — | 0.25 | 0.30 | — | A(2) | 20–25 | 4 | 97 | 88 |
| 3h | D | — | 0.10 | 0.11 | — | A(2) | 20–25 | 5.5 | 100 | 85 |
| 3j | D | — | 0.10 | 0.10 | — | A(2) | 10–15 | 3.5 | 94 | 79 |
| 3k | D | — | 0.10 | 0.10 | — | A(2) | 15–20 | 3 | 89 | 57 |
| 3l | D | — | 0.047 | 0.047 | — | A(2.1) | 25–30 | 8 | 50 | 91 |
| 3m | D | — | 0.25 | 0.29 | — | A(4) | 10–15 | 9.5 | 51 | 71 |
| 6b | D | — | 0.10 | — | 0.102 | A(2) | 41 | 6 | 104 | 84 |
| 6f | D | — | 0.10 | — | 0.11 | A(2) | 30–35 | 3 | 82 | 77 |
| 6i | D | — | 0.11 | — | 0.10 | B(4) | 41 | 4.5 | 102 | 85 |

[a]The conditions, yields and products reported are the result of single runs and are not to be considered optimized.
[b]Catalyst concentrations are reported as mole percent based on the limiting reagent. A = methyltricaprylammonium chloride, B = tetra(n-hexyl)ammonium chloride.
[c]Minimum weight percent obtained by GLC.

TABLE II

Summary of Analytical Data for Products 3 and 6

| Product | $\delta^1HCH_2$[a] | $\delta^{31}P$[b] | $J\ ^{31}PCH$[c] | Purity[d] |  | C (%) | H (%) | N (%) | P (%) |
|---|---|---|---|---|---|---|---|---|---|
| 3a[e] | 3.02 | 22.12 | 22.1 | 81 | Calcd | 54.71 | 9.84 | 4.56 | 10.08 |
|  |  |  |  |  | Found | 54.80 | 9.71 | 4.25 | 9.97 |
| 3b[f] | 3.01 | 22.25 | 22.1 | 94 | Calcd | 59.48 | 10.54 | 3.85 | 8.52 |
|  |  |  |  |  | Found | 59.69 | 10.26 | 3.92 | 8.38 |
| 3c[f] | 3.01 | 22.12 | 22.1 | 95 | Calcd | 59.48 | 10.54 | 3.85 | 8.52 |
|  |  |  |  |  | Found | 59.50 | 10.36 | 3.74 | 8.50 |
| 3d[f] | 3.06 | 21.54 | 22.1 | 97 | Calcd | 61.35 | 10.81 | 3.58 | 7.91 |
|  |  |  |  |  | Found | 61.28 | 11.02 | 3.47 | 8.13 |
| 3e[f] | 3.06 | 21.86 | 22.1 | 95 | Calcd | 61.35 | 10.81 | 3.58 | 7.91 |
|  |  |  |  |  | Found | 61.22 | 11.00 | 3.68 | 7.99 |
| 3g[f] | 2.99 | 22.10 | 22.1 | 96 | Calcd | 63.28 | 10.62 | 3.35 | 7.42 |
|  |  |  |  |  | Found | 63.53 | 11.10 | 3.99 | 7.36 |
| 3h[f] | 3.01 | 22.14 | 22.2 | 94 | Calcd | 62.98 | 11.05 | 3.34 | 7.38 |
|  |  |  |  |  | Found | 63.13 | 11.05 | 3.27 | 7.39 |
| 3j[f] | 3.05 | 21.97 | 22.1 | 96 | Calcd | 62.98 | 11.05 | 3.34 | 7.38 |
|  |  |  |  |  | Found | 63.05 | 10.98 | 3.28 | 7.41 |
| 3k[f] | 3.06 | 21.97 | 22.1 | 88 | Calcd | 62.98 | 11.05 | 3.34 | 7.38 |
|  |  |  |  |  | Found | 63.09 | 11.20 | 3.39 | 7.38 |
| 3l[f] | 3.00 | 19.17 | 21.4 | 91 | Calcd | 62.98 | 11.05 | 3.34 | 7.38 |
|  |  |  |  |  | Found | 63.02 | 11.05 | 3.39 | 7.34 |
| 3m[f] | 2.84 | 24.34 | 20.1 | 91 | Calcd | 65.65 | 11.44 | 2.95 | 6.51 |
|  |  |  |  |  | Found | 65.56 | 11.51 | 3.01 | 6.33 |
| 6b[f] | 2.96 | 48.27 | 15.1 | 91 | Calcd | 65.22 | 11.56 | 4.23 | 9.34 |
|  |  |  |  |  | Found | 66.35 | 11.56 | 4.15 | 8.87 |
| 6f[g] | 2.96 | 47.61 | 14.0 | 100 | Calcd | 66.81 | 11.77 | 3.90 | 8.61 |
|  |  |  |  |  | Found | 66.94 | 11.64 | 3.87 | 8.71 |
| 6i[h] | 2.97 | 48.30 | 14.8 | 85 | Calcd | 68.18 | 11.96 | 3.61 | 7.99 |
|  |  |  |  |  | Found | 68.00 | 12.01 | 3.53 | 7.98 |

[a]$^1$H NMR chemical shift (ppm) of methylene protons signal (center of observed doublet) relative to tetramethylsilane.
[b]$^{31}$P NMR chemical shift (ppm) of the phosphorus atom (decoupled) downfield from 85% phosphoric acid.
[c]$^1$H NMR coupling constant (Hz) for the splitting of the methylene protons signal by the $^{31}$P atom.
[d]Minimum weight percent obtained by GLC.
[e]Prepared by method C; doubled distilled through a 10 cm length Vigreux column.
[f]Prepared by method D; flash distilled, $10^{-3}$ mm Hg (Kugelrohr apparatus).
[g]Prepared by method D; recrystallized from pentane, mp 38.5–40.5.
[h]Prepared by method D; undistilled crude product.

and the stirring rate to 500 rpm. The first product observed (20 min.) by monitoring the progress of the reaction was 3b. However, as the reaction proceeded, another product, eluting earlier than 3b, steadily grew. A large amount of precipitate began to accumulate in the reaction vessel and soon precluded syringe sampling. After a reaction time of 16 hours, 100 ml of water was slowly added to aid dissolution of the accumulated precipitate.

The phases were separated and the aqueous layer washed with 100 ml of methylene chloride. The organic layers were combined and worked up as previously described in Example IV to yield only 12.7 g of an amber oil which was analyzed by GLC and found to be a new product (59%) and 3b (4%). Distillation yielded a fraction 7.9 g, bp 105°-6° (0.35 mm) of a colorless oil which was 93% new product. NMR, IR, and GC-Mass Spec, identified the product as N,N-dibutyl-(n-butoxy)acetamide, 7b.

EXAMPLE VI

This example shows that the processes described herein can be used to prepare novel compounds of the general structure:

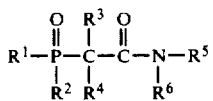

where $R^1$ is alkyl and $R^2$ is alkoxyl.

Preparation of Butyl butyl(N,N-dibutylcarbomylmethyl)phosphinate.

Into a 200 ml three-necked, round-bottom flask equipped with a thermowell, a 125 ml pressure-equalizing addition funnel, a mechanical stirrer, inert gas fittings, and a septum were placed a solution of 10.27 g (0.48 mole) of distilled N,N-dibutylchloroacetamide and 0.86 g (4 mole %) of methyltricaprylylammonium chloride in 40 ml of methylene chloride along with 50 ml of 50% NaOH. The solution was stirred at 250 rpm and maintained at about 15° C. while 9.0 g of a solution which was 85.4% butyl butylphosphonite and 13.7% dibutyl phosphite in 40 ml of methylene chloride was added dropwise under a blanket of nitrogen. Analytical samples were removed by syringe every thirty minutes for GLC analysis to follow the reaction progress by monitoring disappearance of starting material and formation of product. After ninety minutes, all the butyl butylphosphonite had been consumed and a large amount of precipitate began to accumulate in the reaction vessel, making syringe sampling difficult. An additional 1.0 g of the before-mentioned butyl butylphosphonite-dibutyl phosphite solution was added in one portion. After another thirty minutes, the reaction was concluded. With ice-bath cooling, 50 ml of water was added with stirring to dissolve the accumulated solids. The phases were separated and the organic layer washed with two 50 ml portions of water and two 50 ml portions of saturated sodium chloride solution. After drying over anhydrous potassium carbonate, the mixture was filtered and evaporated in vacuo to yield 9.47 g of an amber oil, 26% of which was a mixture of two products, dibutyl N,N-dibutylcarbamoylmethylphosphonate and butyl butyl(N,N-dibutylcarbamoylmethyl)phosphinate. Vacuum distillation (Kugelrohr apparatus) produced a fraction weighing 2.95 g, boiling between 105°-110° C. (at 0.001 mm Hg), which by GLC analysis was 89% of the mixture of the above two products, in a ratio of 78 parts of dibutyl N,N-dibutylcarbamoylmethylphosphonate (by comparison to an authentic sample), representing a 90% yield based on dibutyl phosphite in the starting material, and 22 parts butyl butyl(N,N-dibutylcarbamoylmethyl)phosphinate (by NMR: δCH₂ 2.953 ppm, J ³¹PCH 17.54 Hz) representing a 4% yield based on butyl butylphosphinate in the starting material.

EXAMPLE VII

This example shows the synthesis of DNPAP which is useful in illustrating the utility for improving the extraction of uranium of the process described herein.

Preparation of Dinonylphenyl Acid Phosphate (DNPAP).

Into a one liter three-necked, round-bottom flask fitted with a mechanical stirrer, a thermowell, a pressure-equalizing addition funnel, and inert gas fittings was placed 306.7 g (2 moles) of phosphoryl chloride and 100 ml of anhydrous ethyl ether. To the stirred solution, under a nitrogen atmosphere, was added a solution of 173 g (0.5 mole) of dinonylphenol (Productol Chemical Co.), 40.0 g (0.51 mole) of pyridine, and 200 ml of anhydrous ethyl ether at a rate which permitted maintenance of the reaction temperature at 25° C. by means of an ice bath. When the addition was complete, the mixture was filtered by suction to separate the precipitated pyridine hydrochloride. The filtrate was evaporated in vacuo and the residue dissolved in 120 ml of 1,2-dimethoxyethane. The solution was returned to the reaction flask and to it added, with vigorous stirring, 200 ml of deionized water with maintenance of the solution temperature at 25° C. by means of an ice bath. After completion of the addition, the mixture was stirred an additional hour and the phases allowed to separate. The organic layer was washed with 200 ml of fresh water, then evaporated in vacuo to yield 194.5 g (91%) of a clear viscous amber oil.

EXAMPLE VIII

This example illustrates a laboratory test procedure which can be used to determine the utility of uranium extractants or uranium extractant synergists of any of the products of the process as described herein.

Extraction of Uranium from Wet-Process Phosphoric Acid.

Shake tests were performed using "green" wet-process phosphoric acid (43% P₂O₅) produced in Florida by "OXY Hemihydrate Process" which, after pretreatment with activated charcoal (by the procedure described in B. D. Wells, Treatment of Wet Process Phosphoric Acid with Activated Carbon, paper presented at the ACS National Meeting, Las Vegas, Nev., August, 1980), contained 40 mg/l uranium. The extractant composition being tested was dissolved in Chevron Alkylate 100 (a mixture of alkylbenzenes) to produce the solution concentrations shown in Table III.

The Florida "black" phosphoric acid was pretreated with "Calgon" activated charcoal at ambient temperature to remove organic impurities and produce a "green" acid.

A portion of the green acid was reduced with iron nails to 110-130 mV (measured with a platinum redox electrode) and another portion was oxidized with chlorate to 1100-1115 mV.

A 1:1 volume ratio mixture was made of a sample of each such reacted (i.e. reduced or oxidized) acid, "green" acid and the extractant solution. The sample mixtures were maintained at 40° C. by means of a temperature bath.

The extraction runs were made with the reduced and oxidized acids. The two-phase 1:1 ratio mixtures at 40° C. were shaken for five minutes and allowed to separate. Each phase was analyzed for uranium by neutron activation to calculate the extraction coefficients from reduced acid ($K_{U+4}$) and from oxidized acid ($K_{U+6}$). The acidic extractant used was the product, from Example VII of the reaction of 2,4-dinonylphenol with excess phosphoryl chloride followed by hydrolysis of the nonvolatile product. This extractant is designated DNPAP. DEHPA signifies di(2-ethylhexyl)phosphoric acid. The neutral organophosphorus synergists evaluated in Table III are: trioctylphosphine oxide (TOPO), Di(2-ethylhexyl)N,N-diethylcarbamoylmethylphosphonate (CMP 8822), and (N,N-diethylcarbamoylmethyl)di(n-octyl)phosphine oxide (CMPO 8822).

Run (a) shows the effectiveness for uranium extraction of the acidic organophosphorus extractant, alone, for either $U^{+6}$, from the oxidized acid, or for $U^{+4}$, from the reduced acid.

TABLE III

| Run | Extractant (conc) | $K_{U+4}$ | $K_{U+6}$ |
|---|---|---|---|
| (a) | DNPAP (0.5M) | 5.97 | 1.61 |
| (b) | DNPAP (0.5M) + TOPO (0.125M) | 7.14 | 1.19 |
| (c) | DNPAP (0.5M) + CMP 8822 (0.125M) | 10.4 | 2.02 |
| (d) | DNPAP (0.5M) + CMPO 8822 (0.125M) | 21.5 | 1.85 |
| (e) | DEHPA (0.5M) + TOPO (0.125M) | <0.01 | 0.60 |

Runs (a) and (b) are used as comparison runs. Runs (b) (c) and (d) show the enhanced uranium extraction due to the presence of the indicated neutral organophosphorus synergist.

Similar tests can be made to determine synergistic effect, by replacing the DNPAP with other acidic organophosphorus extractants; however, with some extractants, little or no synergism may be observed with the neutral organophosphorus compounds of runs (b) (c) and (d).

What is claimed is:

1. Process for preparing an organophosphorus compound of the formula (I):

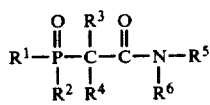
(I)

wherein $R^1$ and $R^2$ can be different or the same and are selected from the group consisting of alkoxyl containing at least 3 carbon atoms, alkyl, aryl, and aryloxyl groups, and wherein $R^1$ and $R^2$ can be in connection forming a heterocyclic ring structure of about 5 to about 7 members including the phosphorus atom; $R^3$, $R^4$, $R^5$ and $R^6$ can be different or the same and are selected from the group consisting of hydrogen, alkyl, or aryl groups and where $R^5$ and $R^6$ can be in connection forming a heterocyclic ring structure of about 3 to about 7 members including the amide nitrogen atom, said process comprising (a) reacting an organophosphorus compound of the formula (II), wherein $R^1$ and $R^2$ are as defined in formula (I):

(II)

with a 2-substituted alkanoic amide of the formula (III):

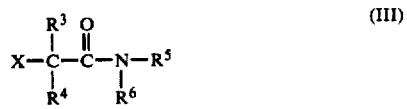
(III)

where X is a good leaving group, and $R^3$, $R^4$, $R^5$ and $R^6$ are as defined as in formula (I); and (b) conducting said reacting in a liquid-liquid, two-phase system comprising an aqueous phase containing a high concentration of an aqueous base and an organic phase containing a phase transfer catalyst and under reaction conditions such that degradative hydrolysis of the products or reactants is substantially avoided and such that said organophosphorus compound of formula (I) is a product of said reaction.

2. Process for preparing carbamoylmethylphosphonates comprising:

(a) reacting (i) a secondary phosphite ester of the formula

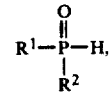

wherein $R^1$ and $R^2$ can be different or the same and are selected from the group consisting of alkoxyl containing at least 3 carbon atoms, or aryloxyl groups, and wherein $R^1$ and $R^2$ can be in connection forming a heterocyclic ring structure of about 5 to about 7 members including the phosphorus atom, with (ii) a 2-substituted alkanoic amide of the formula

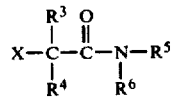

wherein X is good leaving group, and $R^3$, $R^4$, $R^5$ and $R^6$ are the same or different and are selected from the group consisting of hydrogen, alkyl, aryl, and where $R^5$ and $R^6$ can be in connection forming a heterocyclic ring structure of about 3 to about 7 members including the amide nitrogen atom;

(b) conducting said reacting in a liquid-liquid two-phase system comprising an aqueous phase containing a high concentration of (iii) an aqueous base, and an organic phase containing (iv) a phase transfer catalyst under reaction conditions wherein degradative hydrolysis of the product and reactants is substantially avoided and where the carbamoylmethylphosphonate is produced; and (c) recovering said carbamoylmethylphosphonate.

3. The process of claim 2 wherein said reaction conditions include agitation of said two-phase system at a controlled rate such that the rate of the desired reaction is high relative to the rate of said degradative hydrolysis.

4. The process of claim 2 wherein said reaction conditions include conducting said reacting within a temperature range such that the desired reaction proceeds at a rate which produces said carbamoylmethylphosphonate and substantially avoiding degradative hydrolysis of the products and reactants.

5. The process of claim 2 wherein the aqueous phase of said two-phase system has a sufficiently high ionic strength so that distribution of the carbomoylmethylphosphonate, phosphite ester and 2-substituted alkanoic amide to the aqueous phase is not significant, thus preventing appreciable degradative hydrolysis of the organic species.

6. The process of claim 4 wherein said temperature range is between about −20° C. to about 50° C.

7. The process of claim 5 wherein said ionic strength is at least as great as that of a 25% by weight solution of sodium hydroxide in water.

8. The process of claim 2 wherein X is chlorine.

9. The process of claim 2 wherein said phase transfer catalyst is selected from quaternary ammonium compounds and quaternary phosphonium compounds.

10. The process of claim 9 wherein said catalyst has the formula $(Z)_4NX'$ or $(Z)_4PX'$ wherein Z can be the same or different and is selected from alkyl groups containing 1–18 carbon atoms and wherein $X'$ is selected from chloride, perchlorate, hydrogen sulfate, bromide, alkyl sulfate, and alkyl sulfonate, wherein the alkyl group has no more than about 4 carbon atoms.

11. Th process of claim 9 wherein said catalyst has the structure $(Z)_4NX'$ or $(Z)_4PX'$ wherein no more than one Z group is an alkyl group containing less than 4 carbon atoms and the other three Z groups are alkyl groups, which can be the same or different, containing at least 4 carbon atoms.

12. The process of claim 10 wherein said catalyst is selected from methyltricaprylammonium chloride, tetrabutylammonium chloride, tetrabutylammonium hydrogen sulfate, tetrahexylammonium chloride, and tetrabutylphosphonium chloride.

13. The process of claim 2 wherein the 2-substituted alkanoic amide comprises an N,N-dialkylchloroacetamide of the formula:

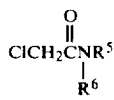

wherein $R^5$ and $R^6$ are the same or different and are alkyl groups of about 1 to about 8 carbon atoms, or can form a heterocyclic ring containing about 5 to about 7 members including the amide nitrogen atom.

14. The process of claim 2 wherein $R^1$ and $R^2$ are selected from the group consisting of primary branched or linear alkoxyl groups of about 4 to 10 carbon atoms, primary linear or branched alkyl groups of from about 1 to about 12 carbon atoms; aryloxy groups which do not impart excessive water solubility to compounds of formula II; and aryl groups that do not impart excessive water solubility to compounds of formula II.

15. The process of claim 14 wherein one of $R^1$ and $R^2$ is aryl and the other is not aryl.

16. The process of claim 2 wherein at least one of $R^3$ and $R^4$ is hydrogen.

17. The process of claim 16 wherein one of $R^3$ and $R^4$ is selected from the group consisting of alkyl groups of about 1 to about 18 carbon atoms.

18. The process of claim 2 wherein one of $R^5$ and $R^6$ is hydrogen and the other is aryl.

19. The process of claim 2 wherein one of $R^5$ and $R^6$ is hydrogen and the other is a linear or branched primary alkyl group containing about 4 to about 18 carbon atoms.

20. The process of claim 2 wherein one or both of $R^5$ and $R^6$ is selected from branched or linear primary alkyl groups containing from about 1 to about 18 carbon atoms.

21. The process of claim 2 wherein $R^5$ and $R^6$ form a heterocyclic ring containing from about 5 to about 7 members including the amide nitrogen atom.

22. The process of claim 2 wherein $R^1$ and $R^2$ are selected from primary branched or linear alkyoxyl groups containing from about 4 to about 10 carbon atoms.

23. A process for preparing an organophosphorus compound of the formula (Ia)

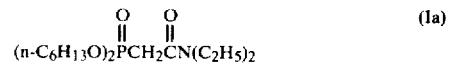

said process comprising
(a) reacting an organophosphorus compound of the formula (IIa) with a 2-substituted alkanoic amide of the formula (IIIa),

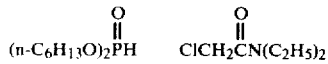

wherein said reacting is conducted at a temperature in the range of about −20° C. to about 40° C. in a liquid-liquid two-phase system comprising a phase transfer catalyst in methylene chloride and an aqueous solution substantially saturated with respect to sodium hydroxide, said reacting being continued for sufficient time for said compound of formula (IIa) to substantially completely react with said 2-substituted alkanoic acid amide of formula (IIIa) to produce a reaction mixture containing said organophosphorus compound of formula (Ia) and for insufficient time for said organophosphorus compound of formula (Ia) to be appreciably degraded, as by hydrolysis said time being determined by analysis of the reaction mixture for said organophosphorus compound of formula (Ia) and degraded products of said organophosphorus compound of formula (Ia); and
(b) recovering said organophosphorus compound of formula (Ia) from said reaction mixture.

* * * * *